(12) United States Patent
Menachery et al.

(10) Patent No.: US 11,358,154 B2
(45) Date of Patent: *Jun. 14, 2022

(54) SYSTEM AND METHOD FOR DETERMINING DIELECTROPHORESIS CROSSOVER FREQUENCIES

(71) Applicant: Precision For Medicine (TX), Inc., Houston, TX (US)

(72) Inventors: Anoop Menachery, Abu Dhabi (AE); Ronald Pethig, Anglesey (GB)

(73) Assignee: Precision For Medicine (TX), Inc., Houston, TX (US)

( * ) Notice: Subject to any disclaimer, the term of this patent is extended or adjusted under 35 U.S.C. 154(b) by 68 days.

This patent is subject to a terminal disclaimer.

(21) Appl. No.: 16/728,474

(22) Filed: Dec. 27, 2019

(65) Prior Publication Data
US 2020/0139382 A1 May 7, 2020

Related U.S. Application Data

(62) Division of application No. 15/302,408, filed as application No. PCT/US2015/023971 on Apr. 2, 2015, now Pat. No. 10,518,273.

(60) Provisional application No. 61/977,356, filed on Apr. 9, 2014.

(51) Int. Cl.
| | |
|---|---|
| *B03C 5/00* | (2006.01) |
| *B03C 5/02* | (2006.01) |
| *G01N 27/447* | (2006.01) |
| *G01N 33/487* | (2006.01) |

(52) U.S. Cl.
CPC .............. *B03C 5/005* (2013.01); *B03C 5/026* (2013.01); *G01N 27/44713* (2013.01); *G01N 27/44721* (2013.01); *G01N 33/48707* (2013.01); *B03C 2201/26* (2013.01)

(58) Field of Classification Search
CPC .......... B03C 5/005; B03C 5/026; B03C 5/028
See application file for complete search history.

(56) References Cited

U.S. PATENT DOCUMENTS

| | | |
|---|---|---|
| 7,063,777 B2 | 6/2006 | Lee et al. |
| 7,169,282 B2 | 1/2007 | Talary et al. |
| 2007/0095669 A1 | 5/2007 | Lau et al. |

FOREIGN PATENT DOCUMENTS

WO    WO-2009034514 A2 *  3/2009

OTHER PUBLICATIONS

Dalton et al., Journal of Applied Microbiology, 2004, vol. 96, pp. 24-32.
Flanagan et al., Stem Cells, 2008, vol. 26, p. 656.
(Continued)

*Primary Examiner* — Alexander S Noguerola
(74) *Attorney, Agent, or Firm* — BakerHostetler

(57) ABSTRACT

The present invention provides a new method for accurately identifying DEP cross-over frequencies of one or more particles in a sample, and quickly and efficiently conveying that information to assist in the separation, e.g., DEP separation, or analysis of the one of more particles under examination or investigation. The present invention also provides an apparatus and method for monitoring the dielectrophoretic response of one or more particles and determining the DEP cross-over frequency of particles of interest.

20 Claims, 10 Drawing Sheets

(56) References Cited

OTHER PUBLICATIONS

Gascoyne et al., Biochimica et BiophysicaActa, 1997, vol. 1323, pp. 240-252.
Gascoyne et al., Isolation of rare cells from cell mixtures by dielectrophoresis, Electrophoresis, 2009, 30, 1388.
Gupta et al., ApoStream, A New Dielectric Device for Antibody independent isolation and recovery of viable cancer cells from blood, Biomicrofluidics 2012, 6, 024133.
Hughes et al., Biochimica et BiophysicaActa, 1998, vol. 1425, pp. 119-126.
International Search Report and Written Opinion in corresponding PCT/US2015/023971 dated Jul. 2, 2015.
Leonard et al., "Explorations of ABO-Rh antigen expressions on erythrocyte electrophoresis: Changes in cross-over frequency," Electrophoresis 2011, 32, 2512-2522 (Year: 2011).
Markx et al., Microbiology, 1994, vol. 140. pp. 585-591.
Pethig et al., Dielectrophoresis: A Review of Applications for Stem Cell Research, Journal of Biomedicine and Biotechnology, 2010, vol. 2010, 182581.
Pethig et al., "Dielectrophoretic detection of membrane morphology changes in Jurkat T-cells undergoing etoposide-induced apoptosis," IET Nanobiotectechnol. 2007, 1 (10), pp. 2-9 (Year: 2007).
Pethig, Review Article—Dielectrophoresis: Status of the theory, technology, and applications, Biomicrofluidics 4, 022811 (2010).
Velugotla et al., Biomicrofluidics, 2012, vol. 6, 044113.
Watarai et al., "Dielectrophoretic Separation of Single Microparticles with Quahdrupole Microelectrode," Chemistry Letters 1998, pp. 279-280 (Year: 1998).

\* cited by examiner

SYSTEM AND METHOD FOR DETERMINING DIELECTROPHORESIS CROSSOVER FREQUENCIES

CROSS-REFERENCE TO RELATED APPLICATIONS

This application is a division of U.S. patent application Ser. No. 15/302,408, filed Oct. 6, 2016, which is a 35 U.S.C. § 371 national phase entry of international PCT Application No. PCT/US2015/023971, filed Apr. 2, 2015, which claims the benefit of priority under 35 U.S.C. § 119(e) of U.S. Provisional Patent Application Ser. No. 61/977,356, filed Apr. 9, 2014, entitled "System And Method For Determining Dielectrophoresis Crossover Frequencies," the entire disclosure of each of which is hereby incorporated by reference.

BACKGROUND

Dielectrophoresis ("DEP") refers to the force experienced by particles suspended in a fluid medium in applied electric field gradients. The dielectrophoretic force is, generally, speaking, the interaction of a non-uniform electric field with the dipole moment it induces in an object. The typical case is the induced dipole in a lossy dielectric spherical particle. The concept of dielectrophoresis has been explained in Pethig, *Review Article—Dielectrophoresis: Status of the theory, technology, and applications*, Biomicrofluidics 4, 022811 (2010). Dielectrophoresis can be used to manipulate, transport, separate, and sort different types of particles. Since biological cells have dielectric properties, dielectrophoresis has many potential medical applications. See, e.g., Pethig et al., *Dielectrophoresis: A Review of Applications for Stem Cell Research*, Journal of Biomedicine and Biotechnology, Vol. 2010, 182581 (doi: 10.1155/2010/182581).

More particularly, DEP may be used for characterizing cells by measuring the changes in their electrical properties. When an electric field gradient is generated, differences in the dielectric polarization between the particles and the fluid medium cause the particles to experience a dielectrophoretic force. This effect can be quantified in terms of the electromagnetic momentum balance via the Maxwell stress tensor, or in terms of the magnitude and distribution of the charges induced on and within the particle by the applied field. Particles, such as blood cells, experiencing strong DEP motion will typically experience a DEP force of about $1 \times 10^{-11}$ N, which is about 40 times greater than the gravitational settling force and about $2 \times 10^5$ times larger than the Brownian diffusion force.

A particle's structural and physico-chemical properties can contribute towards its DEP response. Additionally, the DEP response can also depend on, inter alia, the frequency of the applied electric field. Due to these various dependencies, variations in applied field frequencies and external environment can be used to simultaneously probe different particle substructures and processes. For example, some fundamental electrical properties of cells, such as membrane capacitance, membrane resistance, and cytoplasmic conductance can affect their DEP response. These properties also reflect a cell's ability to maintain ion balances and are a measure of metabolic work and biological organization. Thus, DEP can provide a relatively non-invasive procedure for determining the electrical properties of cell populations, down to the single cell level, and reveal important information about the cells.

The frequency dependence and the direction of the DEP force are governed by the real part of the Clausius-Mossotti factor, which indicates the relative polarizability of a particle with respect to its suspending medium. If a particle, or population of particles, is more polarizable than the suspending medium, then the particle(s) will be attracted to high-intensity electric field regions. This is termed as positive dielectrophoresis (pDEP). Conversely, if a particle, or population of particles, is less polarizable than the suspending medium, the particles will be repelled from the high-intensity field regions, and negative dielectrophoresis (nDEP) occurs. Therefore, the real part of the Clausius-Mossotti factor characterizes the frequency dependence of the DEP force.

Various methods have been developed to measure the DEP cross-over frequency as a function of the conductivity of the suspending medium to provide information for assessing the dielectric properties of suspended particle(s). The DEP cross-over frequency, ($f_{xo}$ or $f_{cross}$), is the transition frequency point where the DEP force switches from pDEP to nDEP, or vice versa. Determination of frequency crossover, cell diameter, along with the conductivity of a suspending solution, provides a measure of cell membrane capacitance. In addition to measurements of crossover frequency, the DEP-induced particle velocity can be measured to assist in characterizing particles. The DEP-induced particle velocity is directly proportional to the DEP force.

Various techniques are available to quantify the dielectrophoretic response of a particle, such as a cell. Systems have been designed to expand and improve applications, efficiencies, reproducibility, and reliability of various types of particle separations, and examinations. See, e.g., Gupta et al., *ApoStream™, a new dielectric device for antibody independent isolation and recovery of viable cancer cells from blood*, Biomicrofluidics 6, 024133 (2012); and Lee et al., U.S. Pat. No. 7,063,777, entitled "Dielectrophoretic Particle Profiling System And Method."

However, large variations in the percentage or degree of separation of particles for a given sample can arise when employing DEP devices. This is because, while there are general guidelines regarding the frequency of the signal that should be employed to separate certain types of particles from others, e.g., certain types of cancerous cells from non-cancerous cells in a sample, in actual practice, particularly in biological applications, there can be significant variation in the voltage frequency that should be employed to separate them from non-target particles in a sample of interest. Thus, in actuality, it can be difficult to obtain a high and consistently reliable degree of separation between target particles and non-target particles. This is particularly important in medical applications, where a consistently high degree of separation of target particles from non-target particles can be critical to accurate medical assessments and treatments of potential patients.

Experimental procedures have been devised in attempts to determine cross-over frequency of particles of interest. These include applying small alternating current (AC) frequency increments or decrements to an applied voltage so that cells in a suspension undergo a cross-over frequency event. Theoretically, the cross-over frequency can be described as the frequency at which a cell undergoes no movement. However, in actual practice, the frequency increments or decrements that are applied can be too large to visually observe the point of no movement of a particle of interest. However, since frequency changes result in either positive DEP (PDEP) or negative DEP (NDEP) and not zero movement, it is difficult to accurately identify the point at which a cross-over event happens.

SUMMARY

The present invention provides a new method for accurately identifying DEP cross-over frequencies of one or more particles in a sample, and quickly and efficiently conveying that information to assist in the separation, e.g., DEP separation, or analysis of the one or more particles under examination or investigation. The present invention also provides an apparatus and method for monitoring the dielectrophoretic response of one or more particles and determining the DEP cross-over frequency of particles of interest. More particularly, the present invention provides a method and system for determining an important electrokinetic parameter of a particle, such as a cell, when, for example, it is suspended in a fluid medium, namely the frequency of an alternating current (AC) electric field at which the electrical impedance of the cell is equal to that of the fluid volume it has displaced. The apparatus or system provided may be employed to capture image sequences of particles under the influence of varying DEP forces and, using image analysis, to determine the response of each particle to the electrical field it is experiencing. The DEP system and method can be used to identify agents that produce a specific response in a cell population or group of particles for the purposes of evaluating drug efficacy, treatment regimens, and performing drug discovery.

These and other aspects of the present disclosure will become apparent to those skilled in the art after a reading of the following detailed description, including the illustrative embodiments, drawing figures, and examples.

DETAILED DESCRIPTION

Figure 1:
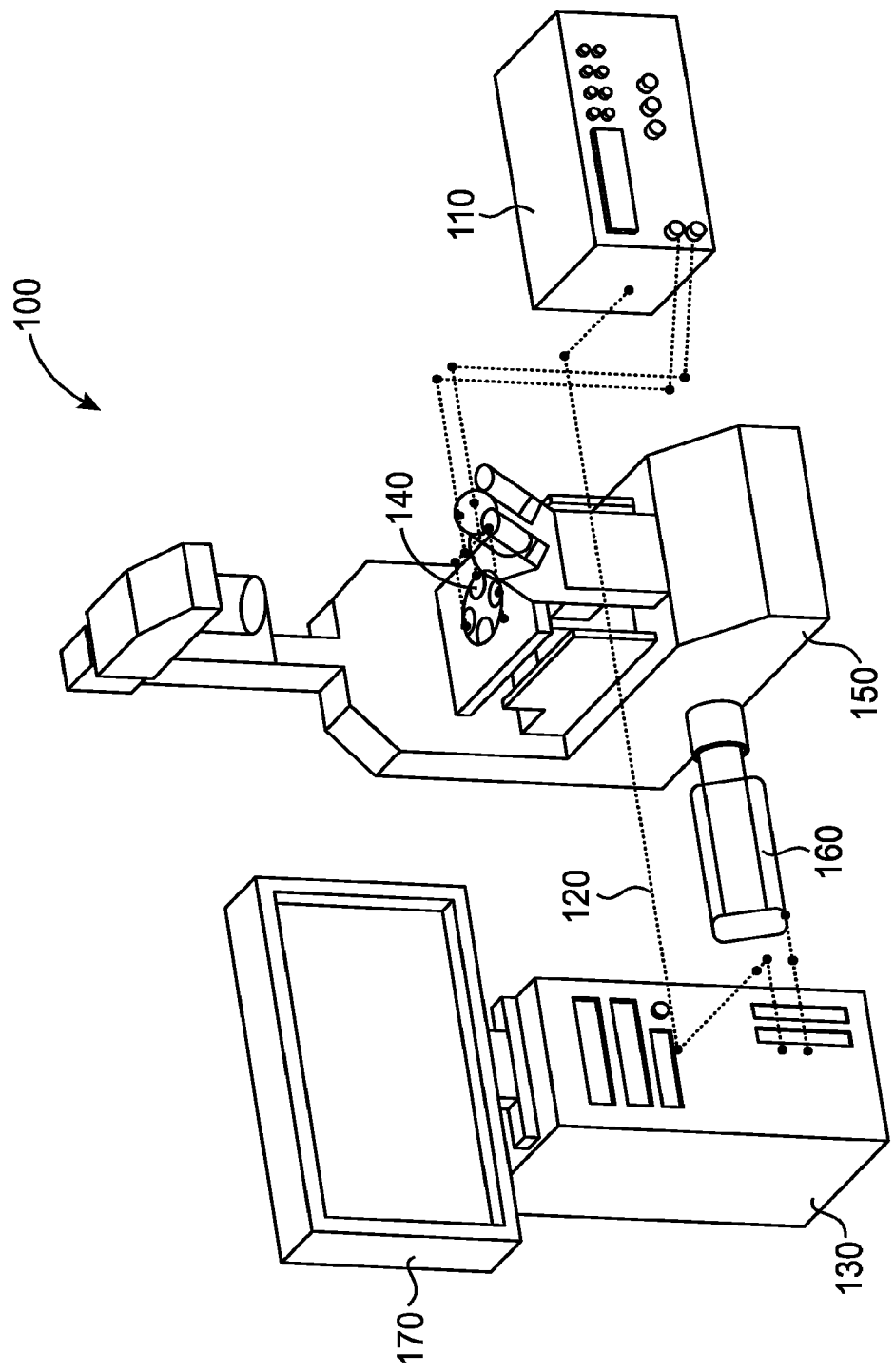
FIG. 1 illustrates a schematic of a dielectrophoretic cross-over frequency analysis platform that may be used in accordance with the present invention.

Dielectrophoresis ("DEP") cross-over frequency ($f_{xo}$) is an electro-kinetic parameter of individual cells that are in a suspension. The DEP cross-over frequency is the point where the DEP force acting on a particle, such as a cell, transitions from a negative to a positive polarity. In the case of a cell, measurement of this frequency and the cell diameter provides a determination of membrane capacitance and is typically observed in the 30~300 kHz range, and more typically observed in the range of 100~300 kHz range.

With all other factors remaining unchanged (e.g., tonicity, osmolarity, pH, and temperature of the suspending fluid), the DEP cross-over frequency exhibited by a mammalian cell generally changes in direct proportion to the conductivity of the suspending medium. For example, if a cell suspended in a medium having a conductivity 30 mS/m (30 millisiemens/meter) exhibits a cross-over frequency of 50 kHz, this value will drop to 25 kHz if the medium conductivity is lowered to 15 mS/m, or rise to 100 kHz if the conductivity is increased to 60 mS/m. In order for a cell to exhibit a DEP cross-over, the medium conductivity should not exceed a value on the order of 100 mS/m. Above this conductivity, the cell will not exhibit a cross-over from negative (−) DEP to positive (+) DEP because the effective polarizability of the cell is less than that of its suspending medium. Even with careful control of the medium's tonicity and osmolarity, the medium conductivity should preferably be above about 15 mS/m in order to reduce the efflux of ions from the cell interior, which can lead to loss of the cell's viability.

With all other factors remaining the same (e.g., conductivity, pH, temperature of the suspending fluid) the DEP cross-over frequency varies in inverse proportion to the size of the cell. Thus, cells of a smaller diameter will generally exhibit a higher cross-over frequency than larger cells of the same type. A change of cell size resulting from cell death as a result of exposure to a toxic chemical agent can also readily be detected as a change in the cross-over frequency.

Again, with all other factors remaining unchanged (e.g., conductivity, pH, temperature of the suspending fluid, as well as cell size) the DEP cross-over frequency generally varies in inverse proportion to the effective capacitance of the plasma membrane of a cell. Membrane capacitance generally increases as a result of an increase of the 'roughness' of the outer surface of the cell membrane, due to the development of membrane folds, microvilli, or blebbing, for example. Thus, cells with minimal complexity of their cell surface topography will exhibit a higher cross-over frequency than cells of the same size having an abundance of surface features such as microvilli or membrane folding. An increase of complexity of a cell's membrane surface can result from exposure to a toxic chemical agent, and this can readily be detected and logged as a function of time as a change in the cross-over frequency. Cancer cells tend to have a more complex membrane surface topography than normal cells.

In recent studies (Flanagan et al, Stem Cells, vol. 26, p. 656, 2008), it was concluded that the differentiation fate of neural stem cells could be predicted by distinct changes in their DEP cross-over frequency before the presence of specific cell-surface proteins (antigens) could be detected. Measurement of the DEP cross-over was also found by Velugotla et al., Biomicrofluidics, Vol 6, 044113, (2012), to provide a means to discriminate human embryonic stem cells from their differentiating derivates.

Microorganisms, such as bacteria and yeast, are more robust than mammalian cells because, unlike mammalian cells, they are protected by a strong cell wall. Bacteria and yeast can therefore be suspended in fluid media of much lower conductivity and osmolarity than is possible for mammalian cells.

In the study of 14 different types of bacteria, Markx et al., (Microbiology, vol. 140, pp. 585-591, (1994)) separated mixtures of Gram-negative and Gram-positive bacteria by dielectrophoresis. For example, when co-suspended in a 280 mM mannitol solution of conductivity 55 mS/m and with an applied 100 kHz voltage signal, *E. coli* exhibited negative DEP and collected in a well-defined region away from the edges of electrodes of a polynomial geometry, whereas *M. lysodeikticus* collected at the edges of these electrodes by positive DEP.

When suspended in an aqueous medium of conductivity 5 mS/m, the herpes simplex virus exhibits a DEP cross-over frequency around 4.5 MHz (Hughes et al, Biochimica et BiophysicaActa, vol. 1425, pp. 119-126, (1998)). Infection of human red blood cells by the malarial parasite *Plasmodium falciparum* can be detected as a change in the DEP cross-over frequency of the cells (Gascoyne et al., Biochimica et BiophysicaActa, vol. 1323, pp. 240-252, (1997)). The electrorotation and DEP characteristics of a range of parasites (e.g., *Ascaris, Cryptosporidium, Cyclospora*, and *Giardia*) has been reported by Dalton et al., (Journal of Applied Microbiology, vol. 96, pp. 24-32, (2004)).

A viable mammalian cell population suspended in an appropriate buffer solution of conductivity of from about 30 mS/m (milli-Siemens per meter) to about 50 mS/m will typically exhibit a DEP cross-over frequency at about 70 kHz to about 300 kHz, and from about 70 MHz to about 300 MHz, as there are two cross-over frequencies for mammalian cells, i.e., for the places where mammalian cells' dielectric properties (low frequency ranges and high frequency ranges (kHz (low) and MHz (high)) equals that of the fluid which is displaced by such cells. Conductivity ranges may be from about 1 mS/m to about 200 mS/m. For example, the conductivity ranges for bacteria are generally much lower than that of mammalian cells. The cross-over determined at the lower frequency can be used to determine the appropriate frequency to be applied to a suspension of cells to, for example, remove peripheral cancer cells from blood. Identification of accurate cross-over frequencies will allow for selectively enriching or separating a subset of target cells, either by attracting a subset of cells to electrodes by positive dielectrophoresis, or repelling them away from electrodes into a fluid flow by negative dielectrophoresis. The high-frequency cross-over appears to be a sensitive indicator of changes in cross-membrane ion flux or of the nucleus-cytoplasm volume ratio. At frequencies above 10 kHz any cell motions resulting from electrophoresis are negligible, and will not influence electro-kinetic measurements, such as dielectrophoresis and electrorotation.

The system and method of this invention, may be used for diverse applications, such as drug discovery, monitoring the viability of cells being transferred from a cryopreserved state to a state wherein they are suitable for study, e.g., room temperature, and determining whether cells are experiencing necrosis or apoptosis. An additional application of the present invention, includes identifying yeast in samples of various beverages, for example, in beer, wine, or other types of alcohol. The present invention may be used, for example, to assist in controlling quality of such averages to determine whether, for a particular sample, a wild strain of yeast has infiltrated the brewing process. Thus, just as the present invention may be used to determine the cross-over frequencies with respect to stem cells, it may also be used to determine the cross-over frequencies of various types of yeast in the preparation of beer—which can be an issue with regard to differences in size of yeast and effervescence of a beer, which is used to provide particular flavor of beer.

In one embodiment of the invention, the present invention provides a method and system for identifying or determining an accurate DEP frequency to be applied to a particle, such as a cell, or population of particles, so that one can quickly and efficiently obtain the particles desired to be studied or analyzed without losing any of the desired particles or attracting other undesired particles. Determining an accurate DEP cross-over frequency in accordance with the present invention allows a substantial amount of cells that are desired to be analyzed, to be pulled out or removed from a separation chamber of a DEP separation system in accordance with the invention at a point where the solution flow is less rapid, and for undesired cells to be pushed further into the chamber where elution flow rate is more rapid and undesired cells are eluted out of the chamber as waste material, which can be recirculated back into the chamber for separating desirable and undesirable cells again.

For example, the method and apparatus of the invention may be used for identifying accurate cross-over frequencies, followed by purifying, enriching, or selecting cells of interest, for example, cancerous cells, and/or separating cancerous cells from non-cancerous cells, from a sample of tissue taken from a patient without substantially damaging or killing the cells of interest, e.g., the cancer cells. In one embodiment, the present invention provides determining the appropriate DEP cross-over frequency for obtaining desired particles, such as cancerous cells from a population of cells, and leaving a majority of undesired particles, such as non-cancerous cells, out of the final product.

Upon determining the appropriate frequency to be applied to a given sample, such as cancerous cells in a tissue sample from a patient or individual, desired particles may then be drawn to electrodes of an electrode element of a DEP separation system while a substantial amount of undesired particles are not drawn to electrodes of the electrode element of a DEP separation system. Thus, the present invention provides a method and system that allows obtaining a high recovery of desired particles, such as from about 60% to about 95%, or higher. The present invention may allow for recoveries on the order of, for example, 65%, 70%, 75%, 80%, 85%, 90% or higher. The present invention also provides an apparatus and method for retesting tested samples in situations where the samples have been identified as having a low recovery of desired particles.

Another aspect of the present invention includes determining and presenting information obtained regarding the movement of particles in response to DEP forces in a quick, efficient, and easily understandable format to a viewer. For example, information obtained may be presented in a graphical presentation including indicia of the tracks or paths that selected cells make as they are induced to move in response to an imposed electric field whose AC frequency is swept from a value below the DEP cross-over frequency to one higher than the DEP cross-over frequency (or vice versa). The track may be exhibited or conveyed to a user of the system through an indicator symbol for quickly and efficiently referencing and recognizing a path or change in path. The indicia employed to identify the DEP crossover points of particles and or their tracks or paths may include pre-designated symbols for presentation to a viewer of the information. Symbols that may be employed include, for example, arrow or 'arrow head'-type symbols (e.g., ↓, ↑, →, ←, >, or <) with a labeled frequency value, such as a DEP cross-over point, at the point of the indicator ('arrow head') giving a precise number for the identified frequency value, or DEP cross-over frequency or point, of a chosen cell in a population of, for example, approximately 40 cells. The present invention creating and identifying an angular measurement to determine and qualify the transition and the frequency associated with the cross-over event.

The present invention provides the means to determine an important electro-kinetic parameter of a cell when it is suspended in a fluid medium, namely the frequency of an alternating current (AC) electric field at which the electrical impedance of the cell is equal to that of the fluid volume it has displaced. In other words, at this particular frequency of a voltage signal applied to electrodes located in a chamber containing a suspended cell or cell population, removal of a cell will not result in a detectable change of the electric field in the chamber or the current drawn by the electrodes. Conversely, when the cell is placed back into the chamber (i.e., the placing of the cell back into a chamber), it cannot be detected electrically. Thus, while the cell is visible to the human eye (via a microscope), it is essentially invisible to the imposed electric field. This essentially means that the target cell does not move by dielectrophoresis, i.e., before that point there is movement in one direction and after that point there is movement in another, e.g., the opposite, direction.

A benefit of the present invention is that when one desires to separate particles, such as cancer cells, in a DEP separation device or system, a voltage oscillator may be employed and, at a frequency below the DEP cross-over frequency (below which the cell is invisible to the electric field and therefore does not respond to the electric field), a cell of interest will either be moving towards or away from an electrode in the device of the invention, depending upon whether one is examining a high frequency cross-over region or a low frequency cross-over region. Generally, at a low-frequency, targets cells will be pushed away from an electrode generating an electric field, and once the DEP cross-over point has been passed the cell will be attracted or drawn to the electrode. Thus, depending on whether one wants to draw target cells to an electrode or push them away from an electrode, the cross-over frequency of the target cells (and non-target cells) is very important to achieving that result.

The size and shape of a particle or cell may be determined by microscopy and, based upon this information, the volume and shape of the displaced fluid may also be determined because it must equal that of the cell. At the cross-over frequency, the dielectric properties of the cell is exactly equal to the volume of fluid that has been displaced. The bulk dielectric properties of the fluid are known or can be measured at this frequency, and from this information we can determine the effective conductivity and dielectric capacitance of the particle or cell. This provides information regarding the physiological state of the cell.

For example, a higher than usual conductivity implies that the outer cell membrane has been compromised, e.g., it has lost its ability to act as an electrical insulator to the passive flow of ions across the membrane. In this regard, viable biological membranes are known to have approximately the same specific capacitance (i.e., capacitance per unit area) of about 1 $mF/cm^2$.

A cell's specific capacitance (capacitance per unit area of the cell membrane) reflects the degree of complexity of the outer morphology of the cell (membrane folds, blebs, microvilli, etc.). Dramatic changes of cell membrane conductivity and capacitance occur on cell death, either by apoptosis or necrosis, for example.

Monitoring and identifying the change of the DEP cross-over frequency of one or more cells, or one or more cells in a population of cells, can thus be employed in accordance with the invention to determine the viability of cells taken from cryopreservation and/or to be used for clinical purposes. The NIH set limits for the viability of cells to be used clinically, but measurement of this involves the invasive use of dyes which can render cells useless for clinical applications. In addition, monitoring and/or identifying the change of the DEP cross-over frequency in accordance with the present invention can also be employed to check or examine the state of differentiation of, for example, stem cells, or following their changes of physiological state without the use of magnetic or fluorescent labels. Moreover, monitoring the change of the DEP cross-over frequency in accordance with the present invention can be employed as a cell-based drug discovery tool through, for example, monitoring the time course of the effects of toxic agents added to a suspension of cancer cells or bacteria.

As explained, at the DEP cross-over frequency, the cell is 'invisible' to the applied electric field. Thus no electrical charges are induced at the interface between the cell and the surrounding fluid medium. In other words, the cell does not take on the properties of an electric dipole moment. At all other frequencies apart from a DEP cross-over frequency the cell will possess an induced dipole moment and exhibit electro-kinetic behavior such as dielectrophoresis (when subjected to a non-uniform field) or electro-rotation (when subjected to a rotating electric field). At its DEP cross-over frequency a cell exhibits neither dielectrophoresis nor electro-rotation.

Collection rate measurements may also be employed to measure positive DEP, whereby electrodes are submerged in a suspension, such as a fluid buffer, with a known concentration of particles and the particles that collect at an electrode are counted. At the DEP cross-over frequency a cell will neither collect at, nor be repelled from, an electrode.

The system of the invention may be used in a number of fields. For example, the system of the invention can be used as a drug discovery tool, e.g., monitoring the dielectrophoretic response of a cell population to candidate chemical compounds. Other potential applications include separating particle populations using their differing dielectrophoretic response. This system can be used to study dielectric particles that are in suspension or that have settled down to the plane of the electrodes by gravitational sedimentation. The particles can be biological or non-biological (i.e., cells, multicellular organisms, polymer/glass microspheres).

The system or apparatus may be used, for example, for profiling of cells, such as: blood cells, including stem cells, white blood cells, red blood cells, and lymph tissue cells; connective tissue cells, such as cells of the bones, cartilage, tendons, and fibrous tissue that support the body organs; epithelial cells from areas of tissue that cover and line the body, the body organs, for example, the organs of the digestive system, and from body cavities, such as the inside of the chest cavity and the abdominal cavity; other organ cells of the body; and cancer cells, tumor cells, precursor cancer and/or tumor cells.

Additional applications that the system and method may be used for include the characterization of blood cell subpopulations on normal blood and the detection of perturbations of those subpopulations resulting from diseases; sample collection (enrichment) for biological warfare agents or pathogens (bacteria, viruses) detection; integrated isolation and molecular analysis of tumor cells; bio-particle fractionation based on dielectrophoretic field-flow fractionation (DEP-FFF) or DEP chromatography; cell patterning for in-vitro cell culture; particle focusing for flow cytometry; single cell manipulation; and detection of molecular binding.

The particles being analyzed can be individual particles or aggregates. If required, particles can be tagged with a fluorescent chemical label to enable identification and examination though fluorescence microscopy. The particles that can be characterized using this DEP invention can vary in diameter from a few micrometers up to a few millimeters, depending on the field gradients that can be generated by the employed electrode geometry. When a fluorescent label is used, submicron-sized particles can be characterized for their DEP properties.

FIG. 1 presents a schematic of one embodiment of components of the system used for the crossover frequency analysis of the invention. As illustrated in FIG. 1, the system 100 includes a signal generator 110 for generating an AC voltage in communication 120 with the control software on a computer 130. The electrodes, generally indicated by 140, can be patterned by means such as photolithography, electroplating and/or laser ablation on an optically transparent substrate of glass or plastic. The electrodes 140 may be positioned in an electrode chamber which is positioned on the microscope 150 for receiving a sample of cell suspension from a patient. Another identifying device maybe employed in place of a microscope. A camera 160 or other image recording device may be attached to or in communication with the microscope 150 for recording images of cells responding to the signal generator 110. The camera 160 and signal generator 110 are illustrated in communication with a computer element 130. The computer element 130 is positioned for synchronizing, receiving, analyzing and relaying information generated by the camera 160 and signal generator 110. The computer element 130 may include a monitor element 170 for displaying information received from the signal generator 110 and or the camera 160.

In operation, a portion of a sample obtained containing, for example, cancerous cells, may be suspended in a solution. An aliquot of the solution (cell suspension), preferably suspended in the same solution as will be used in the DEP separation system, e.g., pH, osmolarity, conductivity, and temperature, is then placed onto a slide containing or in close relationship to the electrode elements. The substrate containing microelectrodes may be placed on the platform of an inverted fluorescence microscope. A sample may be placed on or associated with the electrode element before or after the microelectrode element is placed on the platform. A signal generator is used to supply an AC electrical signal to the microelectrodes. The sample is placed on the electrode platform and, at low electrical frequency, the target cells will move away from the electrodes (i.e., they are moving away from the high field region which is around the electrode edges). Then, at the crossover frequency, the cell(s) of interest pauses, and then once the cross-over frequency has been passed, the cell(s) reverts back to the electrode. This is a primary indicator of cell separation. By identifying or tracing the path of travel of a cell of interest with respect to an electrode element and then measuring the angular displacement of the path or travel of the cell with respect to an electrode, and identifying frequencies associated with each step or point of the path of travel, the combination of these measurements and analyses can be accurately reveal the DEP cross-over point of the cell.

Once this frequency has been determined, it can then be used in a DEP separation system to obtain a high degree of separation between target cells and non-target cells. Thus, for example, where a cross-over frequency is determined to be 40 kHz for one cell type by the method of the invention, and 60 kHz for another cell type, one can accurately determine the frequency of a cell separation system to discriminate between target cells and non-target cells. Accurate cell separation is critical to disease diagnosis and treatment.

If, for example, a cell composition is obtained with a mixture of known or unknown cells, e.g., cancerous cell types, may be respectively tagged, for example, by fluorescence, to assist in determination of cross-over frequencies.

In one embodiment, the applied AC voltage is a sinusoidal waveform. However, other waveforms can also be used including, but not limited to, triangular, saw-tooth, and square waves. An image of the sample, e.g., cells adjacent an electrode, may then be captured using a high-resolution CCD/CMOS camera. The signal generator and camera may be controlled by software loaded on to the CPU of a computer to synchronize the frequency applied by the signal generator with the image identified. The image and frequencies for each step or point in the path of travel of the target particle are recorded during the travel of the particle. Thus, by practicing the present invention one may be able to separate target cells, once the cross-over frequency of the target cells has been determined, in a highly efficient and beneficial way compared to the random sweep approach that is applied with general DEP separation devices.

Figure 2A:
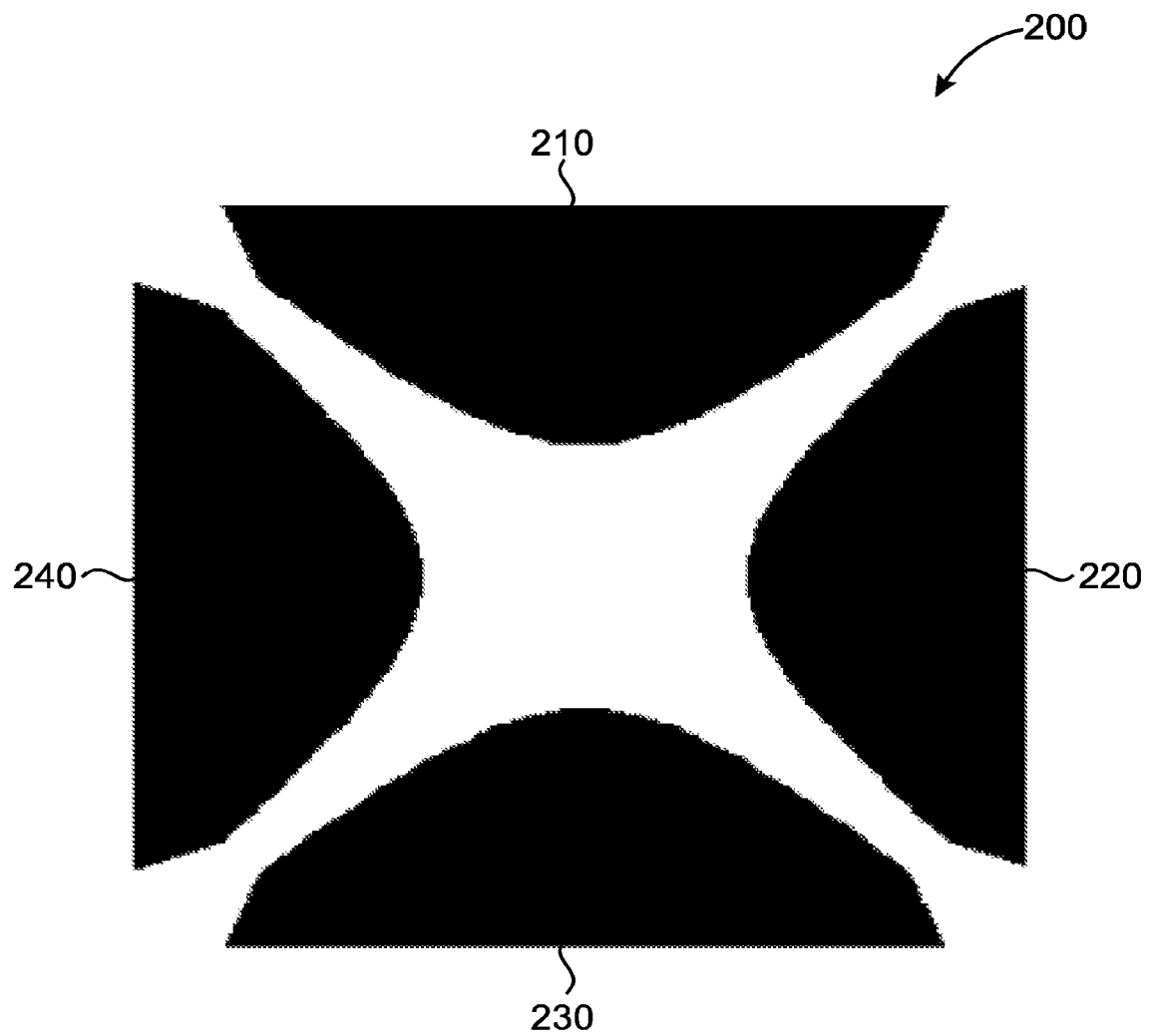
FIGS. 2A and 2B illustrate two embodiments of electrode designs or geometries that may be employed in combination with the platform of FIG. 1 in accordance with the invention.
Figure 2B:
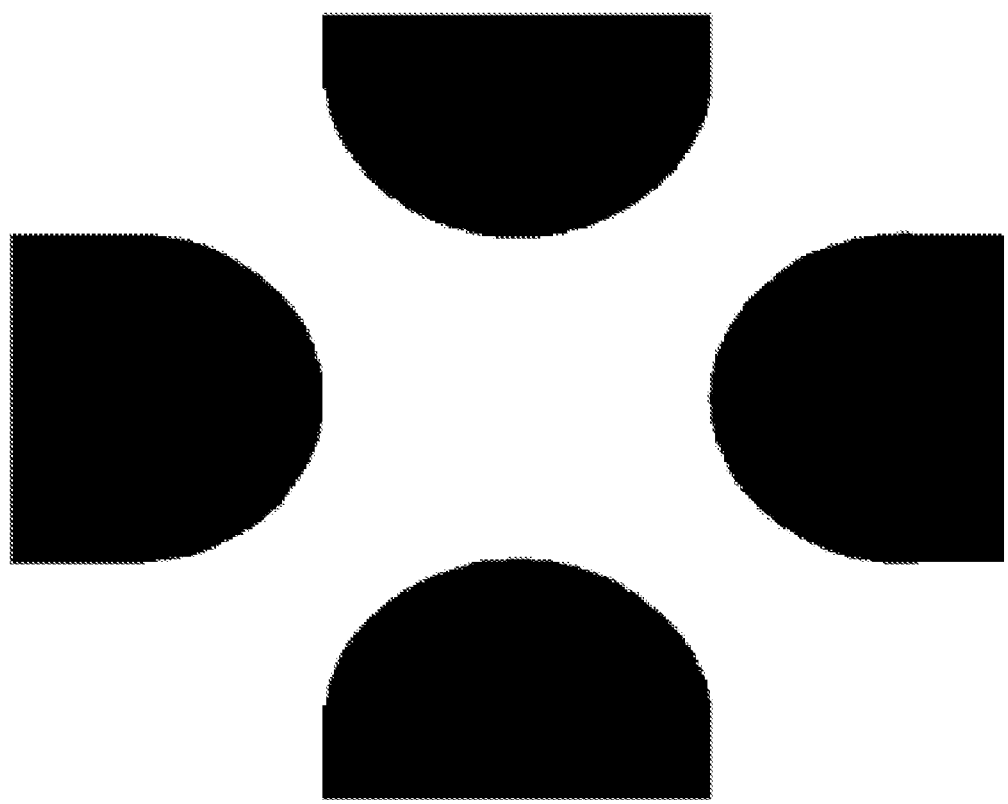
Figure 3A:
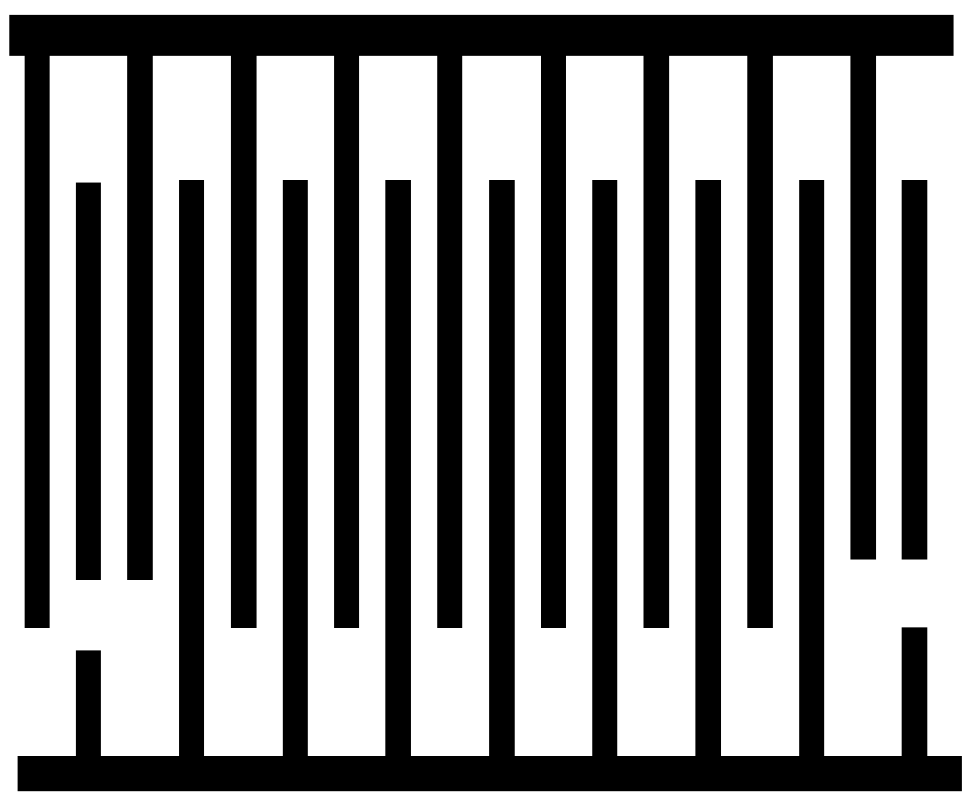
FIGS. 3A and 3B illustrate two further embodiments of electrode designs or geometries that may be used in combination with the platform of FIG. 1 in accordance with the invention.
Figure 3B:
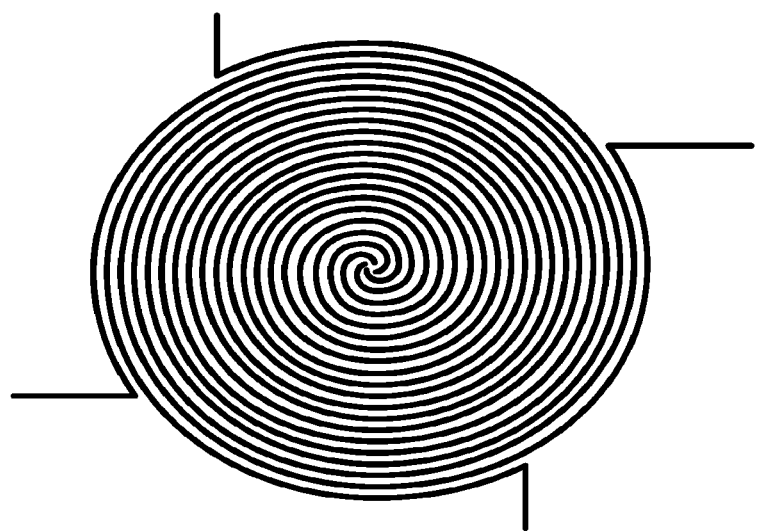

FIG. 2A illustrates an example of a polynomial electrode configuration or design. FIG. 2B illustrates a semi-circular electrode configuration or design. FIG. 3A illustrates an interdigitated electrode configuration or design. FIG. 3B illustrates a spiral electrode design.

Figure 4:
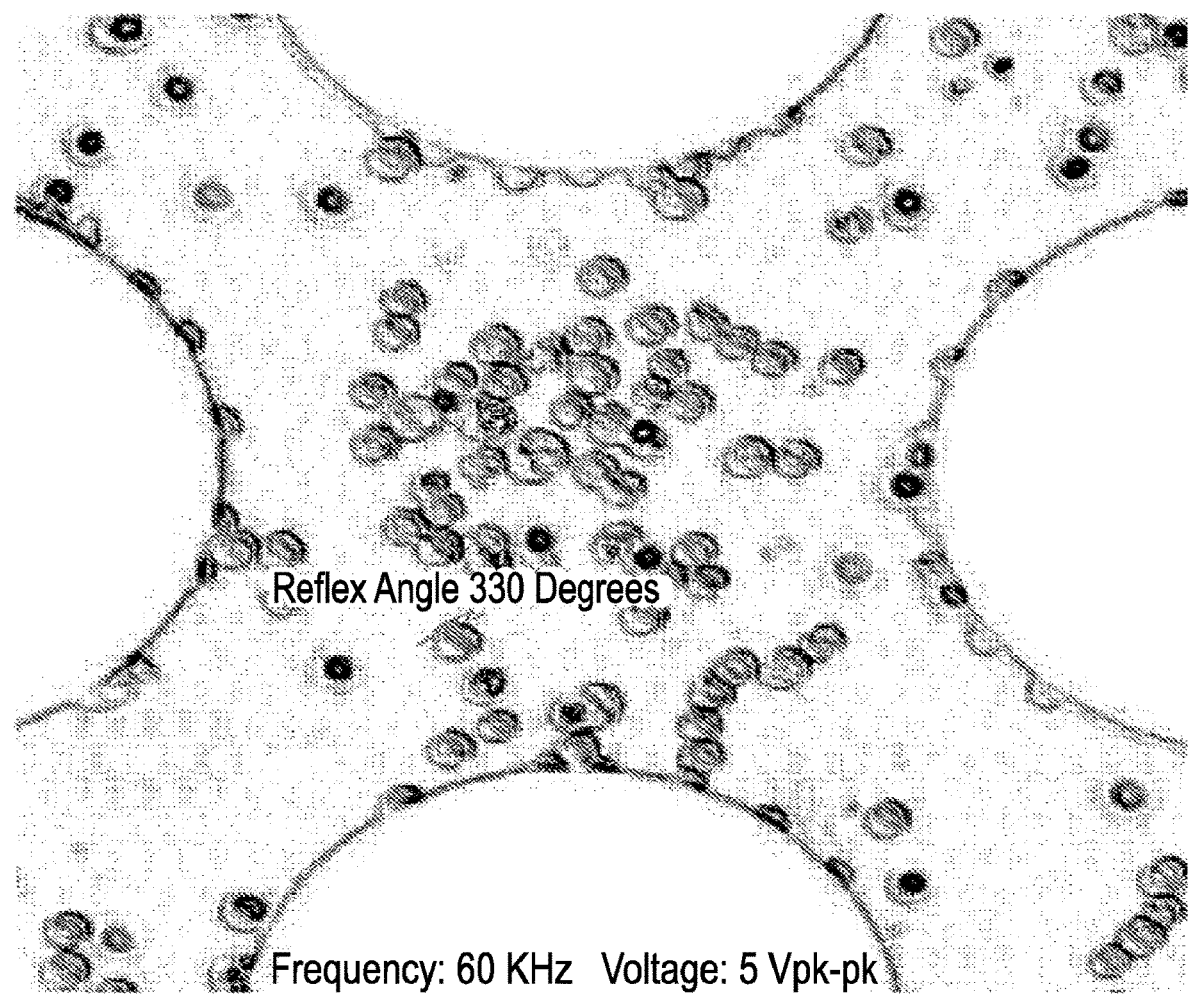
FIG. 4 illustrates another example of part of the method performed on particles subject to dielectrophoretic transition through the cross-over frequency.

As illustrated in FIG. 4, a track (e.g., trace, map, marking, or identifying indicia) is configured to identify the path of movement of one or more particles identified as being of interest, in this case cancer cells or suspected cancer cells (e.g., precancerous cells). The path of the particle may be identified manually, e.g., by hand, for example by identifying target cells of interest and tracing their path of travel, or with the assistance of a computer drawing or tracing program, or it may be performed entirely by a computer assisted procedure (program) designed to identify and track the movement of target cells as explained in accordance with the invention. The path identification of target and/or non-target cells may be performed during or after an electric field or force is or has been applied to a given sample.

For example, a recording or other type of storage or reproduction of the movement of a target particle, such as a video or series of snap shots (e.g., sequential), may be made of the cells in a sample while an electric field is applied to a sample. As the frequency of the electric field is adjusted (increased or decreased), certain cells in the sample under examination will either remain stationary, move toward, or move away from the electrodes generating the non-uniform electrical field. For example, a range of frequencies (or frequency sweep) may be applied, e.g., based upon a known approximate general range for a particular type of particle, e.g., a cancerous cell type, based on information, e.g., general ranges reported in the literature for a given cell type, regarding the sample type under analysis.

Figure 2C:
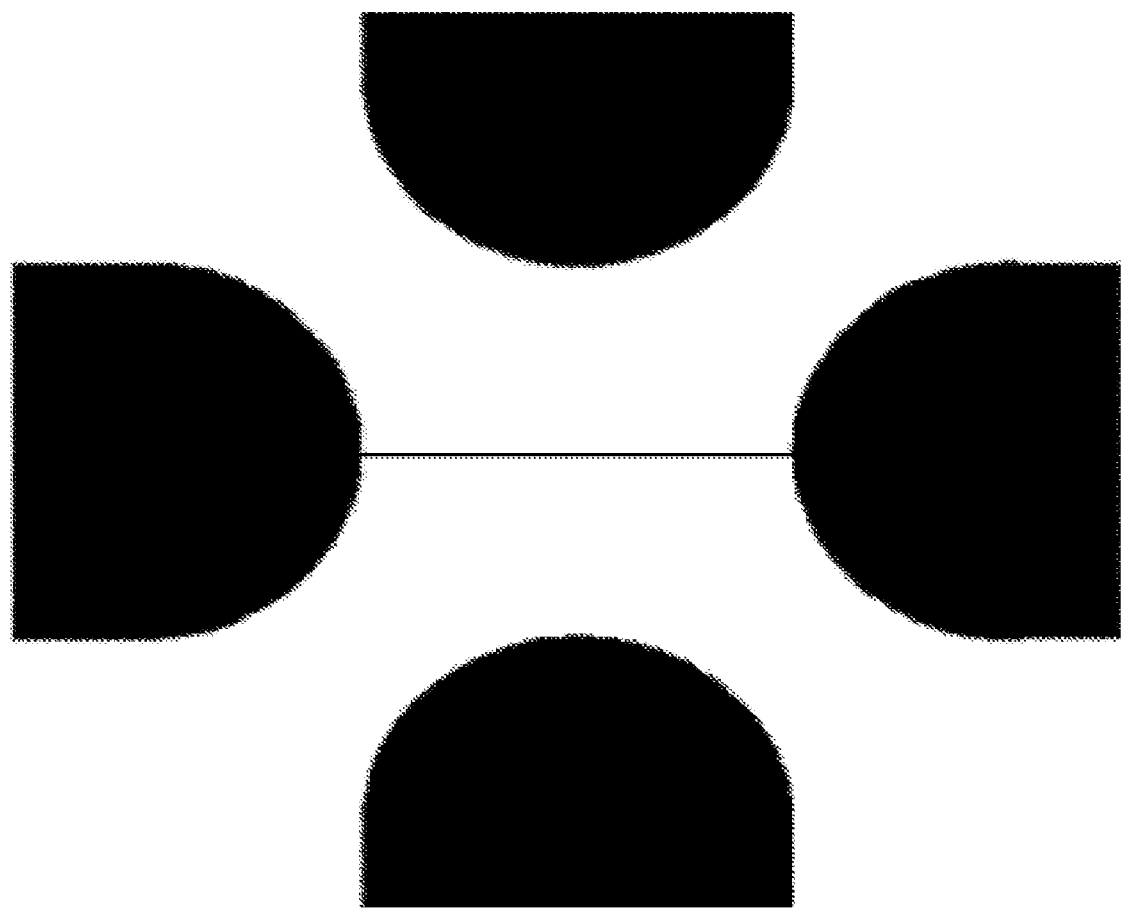
FIGS. 2C, 2D, and 2E illustrate examples of part of the method performed on particles subject to dielectrophoretic transition through the cross-over frequency.
Figure 2D:
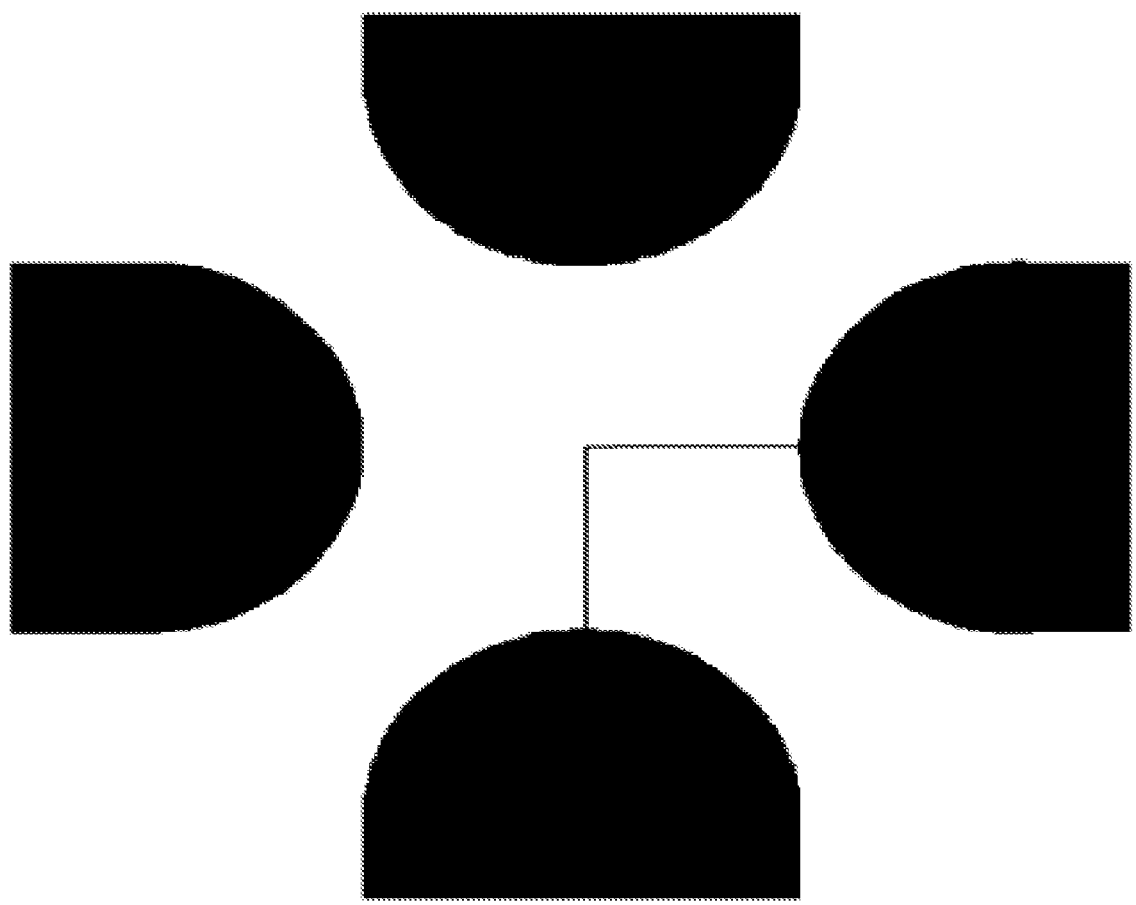
Figure 2E:
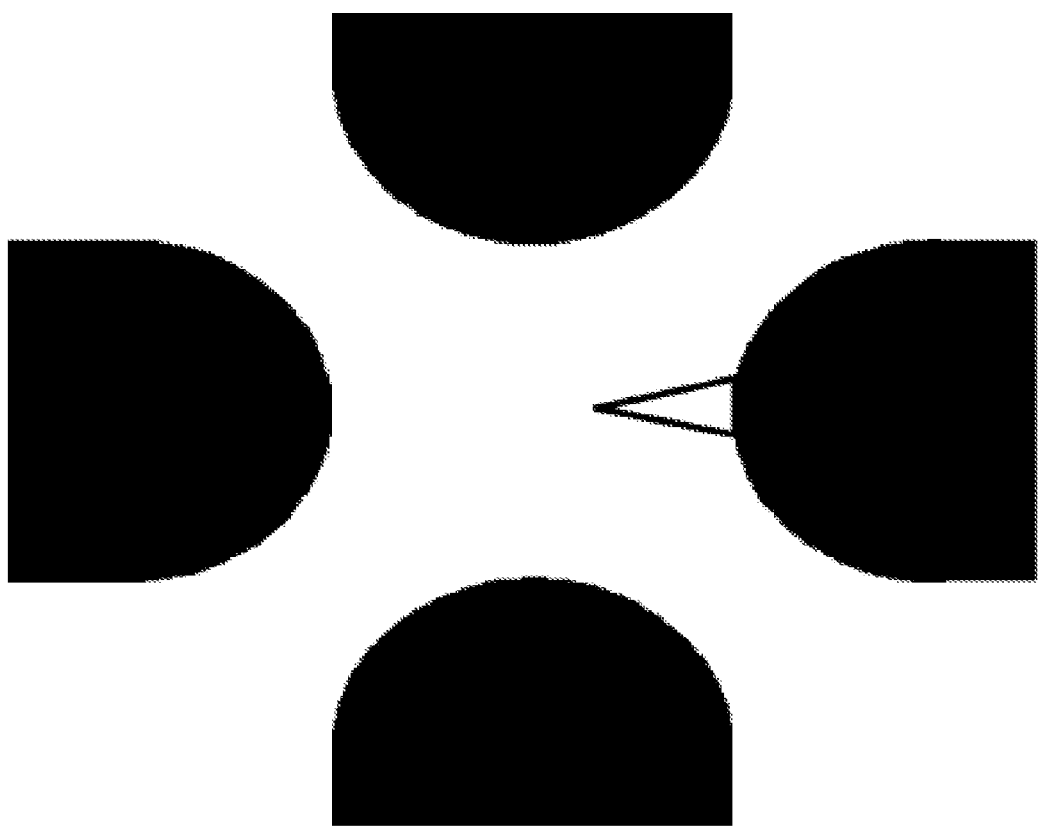

The observed and/or recorded movement of the target(s) is monitored to determine at what points during their travel they moved away from an electrode, stopped, and returned back toward an electrode (same or different). The path of travel of the target(s) is examined to identify the angle that is created by the target during its travel. The movement of the target(s), and in particular the angle of travel, e.g., toward and away from an electrode(s), is used to determine the cross-over frequency of the target(s) (and/or non-target (s)) identified or observed. The frequency applied at the approximate point of stopping, pausing, or slowly turning of the target(s) is the crossover frequency of the target(s). The angle of travel away from and back toward an electrode, or vice versa, is determined. The angle of travel will depend upon various factors such as the number of electrodes employed. For example, as shown in FIGS. 2C and 2D, the travel of the charged particle may be away from one electrode and towards another. In such a situation, where for example two electrodes are positioned at approximately right angles, the reflex angle of travel away from one electrode and toward another may be less than about 270 degrees. If the electrodes are opposite each other, then a charged particle may move from the first electrode across to a second electrode in approximately a straight line.

In a scenario that employs straight interdigitated electrodes, viewed from above, a charged particle may be pushed away from a the right-hand electrode and then be pulled towards an opposite electrode. The most important aspect is the identification of when the particle under consideration pauses or ceases to move during the course of its travel away from and toward an electrode. The determination of the angle of travel is important to quantify the position of movement or transition to obtain a high degree of accuracy and certainty of DEP cross-over frequency, which will then allow for highly efficient and reliable separation of particles in a DEP separation system.

Another object of the present invention is to determine the rate of change of momentum of velocity or speed of the cell, and to detect the points or frequencies where the cell is slowing down and then starts to accelerate again. Thus, in examining, for example, 15 frames of images recorded or observed, and measuring distance traveled by a particle, one can determine velocity at various points of travel of that particle. Thus, both considerations are important: the point or velocity as a function of frequencies when the cell starts to slow down and then accelerate, as well as the points at which the cell changes its direction. Thus, one can detect where the velocity changes and goes through nearly zero ("0") velocity and then begins to increase velocity.

Figure 5:
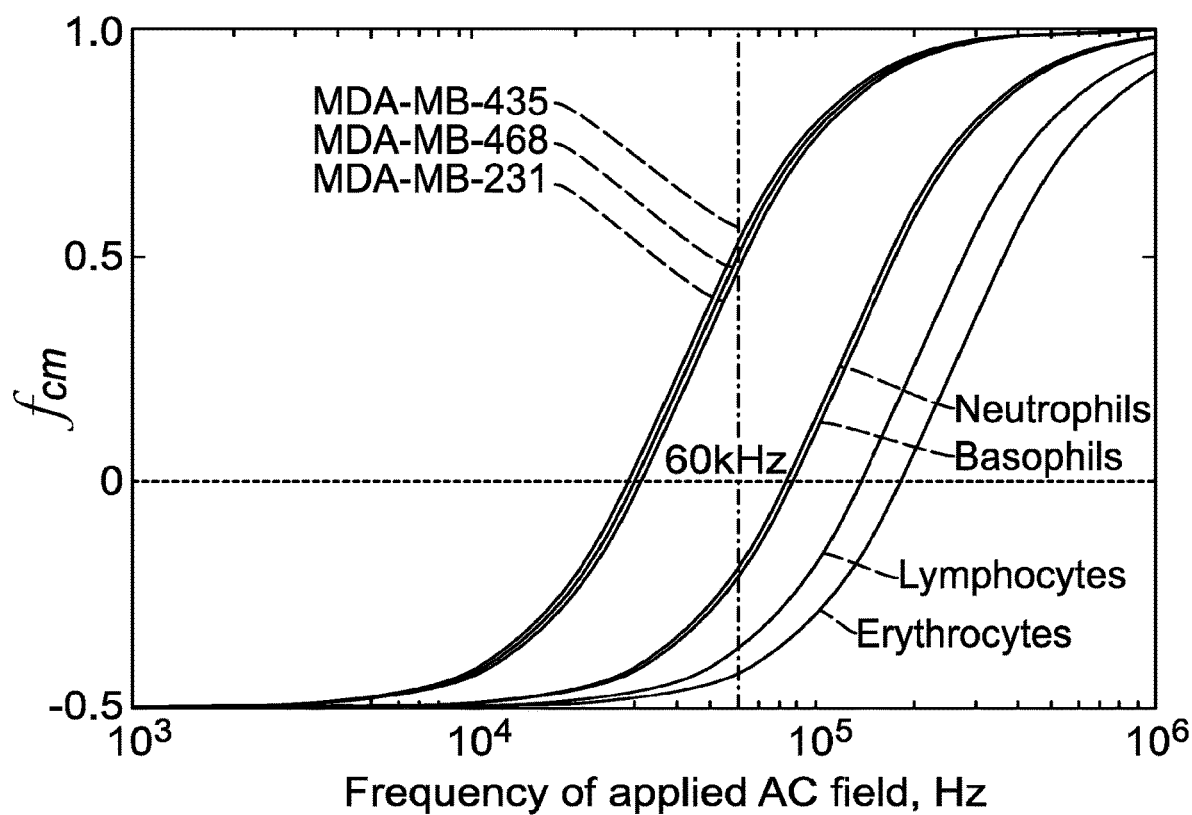
FIG. 5 illustrates, for reference, a general example of a DEP cross-over differentiation schematic or graph of cancerous cells and non-cancerous cells from the journal publication entitled Gascoyne, et al., Isolation of rare cells from cell mixtures by dielectrophoresis, *Electrophoresis*, 30, 1388 (2009).

As shown in FIG. 5, the movement of a particle undergoing a cross-over event with respect to the same electrode may create a reflex angle of travel of from about 200 degrees to about 360 degrees, preferably from about 270 degrees to about 360 degrees, and most preferably at least about 315 degrees to about 360 degrees, from the approximate point and line of origin. The angle of travel will depend in part on the influence of fluid employed in the process. The angle created by a particle of interest is preferably a reflex angle, and preferably is greater than 270 degrees, between two successive displacements or vectors (indicia) which may be used to identify the path of travel to determine the cross-over frequency event.

In an alternate approach, an applied AC frequency may be decreased starting from a value where the particle is expected to undergo positive dielectrophoresis and immobilization on an electrode edge. A frequency sweep in small decrements will result in detachment from the edge of the electrode. The average of two frequencies corresponding to (1) the period of detachment and (2) the period immediately prior to when the particle was still attached to an electrode can be calculated and recorded as the cross-over frequency.

Looking at the central region between the edges of polynomial electrodes, generally identified as 200 in FIG. 2A, a particle that exists at a position of approximately 2 o'clock in the channel between the electrodes 210 and 220 may move towards the center area of the electrode diagram, and be pushed away from the electrode 220. Depending on the amount of fluid flow, for example being based on the coverslip or fluid on the electrodes, a capillary action effect may cause the pulling the liquid slightly one-way, so that when the particle comes to a stop in could still drift slightly and become closer to the electrode 210. That would represent a positive DEP, whereas when it was being pushed away from electrode 220 is negative DEP. Generally, however, cells will return approximately towards the place from where they left or began their travel. Thus, while it may appear or be seen that no sharp angle has been created in the movement, the addition of counter factors, or the creation of angles of about 270° or about 360° may reasonably be said to exemplify the track. In addition, velocity measurements with respect to two opposite electrodes (e.g., 210 and 230, or 220 and 240 of FIG. 2A), the angle will be approximately 180°. Then it can be determined where the velocity of the particle is the least and the particle appears to stop moving, which will be identified as the cross-over frequency. Thus comparing the velocities to the frequencies may assist in determining the DEP cross-over frequency point.

Alternatively, when a particle is undergoing negative DEP frequency it is below the crossover line, as illustrated in FIG. 5. So the velocity is directly proportional to the CM factor; so when it is −0.5 the velocity is at its highest and the part was being pushed away from the electrode. Now where the DEP is being swept to a point where it undergoes positive DEP, velocity continually slows down to a point where it is almost 0 and then again it begins to speed up. Thus, the rate of displacement can be measured and when that event takes place that can also be denoted as a cross-over frequency.

This approach can be carried out using a frequency sweep in small increments starting from a value below the expected cross-over frequency. Velocity is measured between successive points of displacement and a minimum is identified. For example, if 6 successive displacements are measured at equal time intervals, and the in displacements 3-4 the displacement is less than for 1-2, 2-3, 4-5 & 5-6, then a minimum velocity region corresponding to the DEP cross-over frequency event has been identified. The average of the frequencies corresponding to points 3 and 4 can be identified and recorded as the cross-over frequency.

In addition, when using interdigitated electrodes, one electrode can be set at a different frequency to an adjacent electrode. Thus, if one electrode is operating slightly higher (e.g., 10 kHz higher) than the other one, there is a set voltage frequency difference which can operate at the same time and be swept in frequency together, maintaining the frequency difference between them. This would be a situation where, for example, cells can be seen being pushed away from both electrodes, which corresponds to both electrodes operating below the crossover, to a point where suddenly they are being attracted to just one electrode and repelled from the other. The cross-over frequency would be between the two frequencies being applied. As frequency increases or sweeps slightly higher all of the cells would be attracted to all of the electrodes. This is because both electrodes would be operating above the cross-over frequency.

As exemplified in FIG. 4 which is an example of part of the method of the invention, a reflex angle of approximately 330 degrees is drawn for a single target cell indicating that the point of DEP cross-over frequency (the point where the cell paused in its movement) has been passed for a particular cell and the cell is returning toward the electrode. As an alternate to identifying a reflex angle measurement, acute or obtuse angles can also be used as a determining factor for a cross-over frequency event.

Computer software may be employed to control the waveform to the electrode and the camera of the present invention which records the movement of target particles. A sweep of frequency may be applied so that target cells move from a frequency that induces negative DEP to positive DEP or vice versa. For accurate crossover frequency determination, the frequency increments/decrements should be approximately 10 kHz or lower. The path of the cells of interest tracked can then be saved on a reproducible medium, such as a storage member of the computer program, and then the images may be analyzed to track the movements of various cells, particularly target cells, if this procedure is not done during the actual process when the electrical field is applied. Frequencies may be identified and correlated or assigned to each point of the cell(s) travel. One may use software (e.g., ImageJ®) to assist in reporting the movement of target cells which may then be tracked manually and after, for example, approximately at 10 frames of images, the movement of target cells tracked may be identified to determine their angular displacement with regard to one or more electrodes. Angles are created by displacement vectors based on the path of travel of target cells. A displacement between two reflex vectors greater than 270°, e.g., 360 degrees back to the electrode, can be used to determine the point at which there is a cross-over frequency transition. The average of two frequencies immediately prior to and subsequent to where the particle undergoes a DEP transition can be calculated to be the crossover frequency.

As illustrated in FIG. 5, the real part of the Clausius—Mossotti factor (fcm) (the y axis (force on cells from field)) is plotted as a function of the frequency of the applied AC field in Hertz (Hz) (the x axis). As an example, three cancerous cell lines (MDA-MB-435, MDA-MB-468, and MDA-MB-231 are shown to exhibit a crossover frequency between 10 and 20 kHz. As can be seen, at 60 kHz the cancerous cell lines can be distinguished for separation from the non-cancerous cell lines. At the zero point on the y-axis there is no force being exerted on the cells, so the net force is zero. Below zero point on the y-axis the net force is negative, meaning the cells are being pushed away from the electrodes. As frequency increases, the negative force begins to diminish, and the force becomes positive whereby cells move towards or become attracted to the electrode. Thus, by determining the cross-over frequency of cancerous cells with respect to the cross-over frequency of non-cancerous cells, we can determine at what point cancer cells are attracted to electrodes while non-cancerous cells are repelled or relatively repelled by electrodes. The present invention provides a method for accurately determining that value. Normal cells will be generally analyzed at a range of 85 kHz to about 220 kHz. Particularly preferred is identifying particular cells or causing an angle of travel of about 270 degrees to about 360 degrees to be created.

In one embodiment, the invention is generally directed to the determination of cross-over frequency of a target cell(s) or particle(s) of interest. As explained, a sample containing a target particle(s) or particles of interest is exposed to an electric field. The electric field frequency applied to the sample may be a range (e.g., a sweep) that encompasses at least one cross-over frequency of one or more particles of interest. The movement of the target particle is monitored to identify its movement away from and then back toward (or vice versa) an electrode generating an electrical field. An assessment is made to determine the angle of travel during the movement of a particle of interest with regard to an electrode and to determine the approximate point at which a particle of interest pauses in its movement with respect to the electric fields or currents applied to the particle.

After at least one cross-over frequency of the particle of interest (or target particle) has been determined, the particle cross-over frequency that has been determined may then be used to calibrate or set an appropriate DEP frequency in a DEP separation device for a sample containing similar or same-type of particles of interest (e.g., particles having common physical and/or chemical properties). The practice of these steps will yield a more efficient and reliable separation of target particles from non-target particles in a sample than would otherwise be possible.

Thus, in practice, one particular embodiment of the invention includes obtaining a sample or composition that contains cancerous cells and non-cancerous cells. Generally speaking, cancerous cells will have DEP cross-over frequencies that are different from non-cancerous cells because of their physical characteristics, e.g., shape, size, and cell membrane texture. A portion of the sample may be separated from the sample obtained and cancerous cells in the portion may be then be treated to distinguish them from the non-cancerous cells, such as by labeling, e.g., fluorescence, according to procedures known in the art. The sample portion containing the distinguished cancer cells may then be applied to an electrode containing element, such as shown in FIGS. 1-4, and an electric field is then applied to the sample portion via the electrodes. The electric field applied to the sample portion maybe a range or sweep, e.g., low-high, or high to low, that encompasses the cross-over frequency of the cancer cells in the sample portion based on information known in the art regarding the approximate cross-over frequencies of a particular type of cancer cell. As explained, the movement of the cancer cells due to the electric field may be observed and/or recorded for analysis. The path of movement of the cancer cells away from an electrode before the cross-over frequency has been reached and back towards an electrode after the cross-over frequency has been reached may then be traced to determine the point of cross-over frequency, or approximate point of cross-over frequency, at which the cancer cells paused in their movement during travel away from and back towards an electrode. The frequency for non-cancerous cells will typically be about 85 kHz to 220 kHZ. The angle defined by the line of travel away from an electrode and then back towards the electrode after the cell pauses is then defined. As explained, if the angle is, for example, of about 270 degrees or more (reflexive), then it can be assumed that the DEP cross-over frequency has been identified as the frequency at which the cancer cell paused in its movement in its travel away from an electrode before returning back to an electrode. At a frequency that is below the crossover frequency of a particle, the particle experiences negative DEP forces and is pushed away from high field regions into the gap between electrodes. As applied frequency increases, and if particle is halfway between 2 opposing electrodes when the frequency is at the crossover frequency, it may become positively attracted to the opposing electrode and continue in a straight line path. In this case, crossover frequency can be determined by determining the point at which the velocity of the particle is a minimum.

The type(s) of cells that may be analyzed, whether in cancerous form or not, include salivary gland, mucous cell, salivary gland number 1, Von Ebner's gland cell in tongue, mammary gland cell, acrimal gland cell, ceruminous gland cell in ear, eccrine sweat gland dark cell, eccrine sweat gland clear cell, apocrine sweat gland cell, gland of Moll cell in eyelid, sebaceous gland cell, Bowman's gland cell in nose, Brunner's gland cell in duodenum, seminal vesicle cell Prostate gland cell, Bulbourethral gland cell, Bartholin's gland cell, Gland of Littre cell, Uterus endometrium cell, isolated goblet cell of respiratory and digestive tracts, stomach lining mucous cell, Gastric gland zymogenic cell, Gastric gland oxyntic cell, Pancreatic acinar cell, Paneth cell of small intestine, Type II pneumocyte of lung, Clara cell of lung, Hormone secreting cells, Anterior pituitary cells, Somatotropes, Lactotropes, Thyrotropes, gonadotropes, Corticotropes, Intermediate pituitary cell, secreting melanocyte-stimulating hormone, Magnocellular neurosecretory cells, secreting oxytocin cells, secreting vasopressin cells, Gut and respiratory tract cells, secreting serotonin cells, secreting endorphin cells, secreting somatostatin cells, secreting gastrin cells, secreting secretin cells, secreting cholecystokinin cells, secreting insulin cells, secreting glucagon cells, secreting bombesin cells, Thyroid gland cells, thyroid epithelial cells, parafollicular cells, Parathyroid gland cells, Parathyroid chief cells, Oxyphil cells, Adrenal gland cells, chromaffin cells, secreting steroid hormones cells (mineralcorticoids and gluco corticoids), Leydig cell of testes secreting testosterone, Theca interns cell of ovarian follicle secreting estrogen, *Corpus luteum* cell of ruptured ovarian follicle secreting progesterone, Granulosa lutein cells, Theca lutein cells, Juxtaglomerular cell (renin secretion), *Macula densa* cell of kidney, Peripolar cell of kidney, Mesangial cell of kidney, Derived primarily from ectoderm, Integumentary system cells, Keratinizing epithelial cells, Epidermal keratinocyte, Epidermal basal cell (stem cell), Keratinocyte of fingernails and toenails, Nail bed basal cell (stem cell), Medullary hair shaft cell, Cortical hair shaft cell, Cuticular hair shaft cell, Cuticular hair root sheath cell, Hair root sheath cell of Huxley's layer, Hair root sheath cell of Henle's layer, External hair root sheath cell, Hair matrix cell (stem cell), Wet stratified barrier epithelial cells, Surface epithelial cell of stratified squamous epithelium of cornea, tongue, oral cavity, esophagus, anal canal, distal urethra and vagina, basal cell (stem cell) of epithelia of cornea, tongue, oral cavity, esophagus, anal canal, distal urethra and vagina, Urinary epithelium cell (lining urinary bladder and urinary ducts), Nervous system, nerve cells, also known as neurons, Sensory transducer cells, Auditory inner hair cell of organ of Corti, Auditory outer hair cell of organ of Corti, basal cell of olfactory epithelium (stem cell for olfactory neurons), Cold-sensitive primary sensory neurons, Heat-sensitive primary sensory neurons, Merkel cell of epidermis (touch sensor), Olfactory receptor neuron, Pain-sensitive primary sensory neurons, Photoreceptor cells of retina in eye, Photoreceptor rod cells, Photoreceptor blue-sensitive cone cell of eye, Photoreceptor green-sensitive cone cell of eye, Photoreceptor red-sensitive cone cell of eye, Proprioceptive primary sensory neurons, Touch-sensitive primary sensory neurons, Type I carotid body cell (blood pH sensor), type II carotid body cell (blood pH sensor), Type I hair cell of vestibular system of ear (acceleration and gravity), Type II hair cell of vestibular system of ear (acceleration and gravity), Type I taste bud cell, Autonomic neuron cells, Cholinergic neural cell, Adrenergic neural cell, Peptidergic neural cell, Sense organ and peripheral neuron supporting cells, Inner pillar cell of organ of Corti, Outer pillar cell of organ of Corti, Inner phalangeal cell of organ of Corti, Outer phalangeal cell of organ of Corti, Border cell of organ of Corti, Hensen cell of organ of Corti, Vestibular apparatus supporting cell, Taste bud supporting cell, Olfactory epithelium supporting cell, Schwann cell, Satellite glial cell (encapsulating peripheral nerve cell bodies), Enteric glial cell, Central nervous system neurons and glial cells, Astrocytes, neuron cells, Oligodendrocyte, Spindle neuron, Lens cells, Anterior lens epithelial cell, Crystallin-containing lens fiber cell, Derived primarily from mesoderm, Metabolism and storage cells, Hepatocyte, Adipocytes, White fat cell, Brown fat cell, Liver lipocyte, Barrier function cells (lung, gut, exocrine glands and urogenital tract), kidney, Kidney parietal cell, kidney glomerulus podocyte, Kidney proximal tubule brush border cell, Loop of Henle thin segment cell, Kidney distal tubule cell, Kidney collecting duct cell, Type I pneumocyte, Pancreatic duct cell (centroacinar cell), Nonstriated duct cell (of sweat gland, salivary gland, mammary gland, etc.), principal cell, Intercalated cell, Duct cell (of seminal vesicle, prostate gland, etc.), Intestinal brush border cell (with microvilli), Exocrine gland striated duct cell, Gall bladder epithelial cell, Ductulusefferensnonciliated cell, Epididymal principal cell, Epididymal basal cell, Extracellular matrix cells, meloblast epithelial cell, Planumsemilunatum epithelial cell of vestibular system of ear (proteoglycan secretion), Organ of Corti interdental epithelial cell (secreting tectorial membrane covering hair cells), Loose connective tissue fibroblasts, Corneal fibroblasts (corneal keratocytes), Tendon fibroblasts, Bone marrow reticular tissue fibroblasts, non-epithelial fibroblasts, pericyte, Nucleus pulposus cell of intervertebral disc, Cementoblast/cementocyte, odontoblast/odontocyte, Hyaline cartilage chondrocyte, Fibrocartilage chondrocyte, Elastic cartilage chondrocyte, Osteoblast/osteocyte, Osteoprogenitor cell (stem cell of osteoblasts), Hyalocyte of vitreous body of eye, Stellate cell of perilymphatic space of ear, Hepatic stellate cell (Ito cell), Pancreatic stelle cell, Contractile cells, Skeletal muscle cells, Red skeletal muscle cell, White skeletal muscle cell, Intermediate skeletal muscle cell, nuclear bag cell of muscle spindle, nuclear chain cell of muscle spindle, Satellite cell (stem cell), Heart muscle cells, Ordinary heart muscle cell, Nodal heart muscle cell, Purkinje fiber cell, Smooth muscle cell, myoepithelial cell of iris, myoepithelial cell of exocrine glands, Blood and immune system cells, Erythrocyte, Megakaryocyte (platelet precursor), Monocyte, Connective tissue macrophage, Epidermal Langerhans cell, Osteoclast, Dendritic cell, microglial cell (in central nervous system), Neutrophil granulocyte, Eosinophil granulocyte, Basophil granulocyte, Hybridoma cell, Mast cell, Helper T cell, Suppressor T cell, Cytotoxic T cell, Natural Killer T cell, B cell, Natural killer cell, Reticulocyte, Stem cells and committed progenitors for the blood and immune system, Germ cells, Oogonium/Oocyte, Spermatid, Spermatocyte, Spermatogonium cell (stem cell for spermatocyte), Spermatozoon, Nurse cells, Ovarian follicle cell, Sertoli cell (in testis), Thymus epithelial cell, Interstitial cells, Interstitial kidney cells, viruses such as Rhinoviruses, Rotaviruses, Influenza viruses, Herpes Simplex Viruses and Human Papilloma Virus, bacteria such as Normal Flora, Nucleic Acids such as DNA and RNA and Proteins.

The cross-over frequency determined for the sample portion may then be used to calibrate or set the frequency of an electric field to be employed in a DEP separation device, e.g., the ApoStream® DEP separation system. A remaining portion of the original sample obtained may then be prepared for use in the DEP separation system and run through the DEP separation system to accurately and efficiently separate cancer cells from non-cancerous cells.

Where multiple samples are obtained from a patient based on a periodic evaluation or ongoing basis, it will generally be advisable to reassess periodically, e.g., monthly, etc., a new sample from the same patient to assess whether there have been changes in the morphology or physiology, genotype, phenotype of the cancer being assessed, and whether the treatment should be altered. Such changes to the disease state may have an effect on such cross-over frequencies and, therefore, diagnoses or relative treatment methods of such cancer. Thus, for instance, where there are types of cancer cells that do not take up labeling efficiently or sufficiently to enable detection to a reasonable degree to make determinations, the method of the present invention can help to distinguish between various types of cancer cells based on dielectrophoretic cross-over frequency determinations.

Separation efficiencies obtained may be on the order of greater than 60% such as between from about 60% and about 95%, or from about 65% to about 90%, or from about 70% to about 85%. Preferably, the efficiency of separation of target particles will be at least about 70%, and more preferably at least about 80%. As can be appreciated, separation efficiency and consistency can be very important to designing effective medical treatments.

Preferably the electrodes are microelectrodes that are planar in shape or design. Planar microelectrodes connected to the signal generator enable characterization of dielectrophoretic (DEP) responses of various samples, e.g., cell types, and other particles. The electrodes may be patterned as approximately 100 nm thick coatings of gold on an approximately 3 nm thick titanium seed layer on one flat surface of a 2" glass wafer using photolithography and metal vapor deposition. As one of ordinary skill the art can appreciate, numerous other embodiments of electrodes are possible in accordance with the present invention.

Preferably, the electrode pattern consists of 4 electrodes with curved tips arranged to oppose each other at a radial angular spacing of 90° as shown in FIG. 2 where the curvature of the electrode tip obeys a polynomial function (FIG. 2A), or is of a simple semicircular shape as shown in FIG. 2B. When the DEP cross-over frequency of mammalian cells is to be determined, the minimum distance between opposing electrode tips should be approximately 100 microns. The maximum inter-electrode spacing should generally not be more than about 5 millimeters. Increasing the spacing between electrodes allows for a larger number of cells or particles to be imaged and characterized at the same time. However, this advantage has to be balanced against the requirement that a larger magnitude of an applied voltage signal would be required as the inter-electrode spacing is increased. For the electrode design shown in FIG. 2A the inter-electrode spacing is about 400 microns. In FIG. 2B the inter-electrode spacing is about 200 microns.

FIG. 2C illustrates an example where a particle moves directly, or nearly directly, across from one electrode to another electrode. This angle of movement may be 0 degrees or 180 degrees, depending upon one's perspective. In the middle there is an electrode generated field which is at a minimum, and at the edges close to the electrodes there is an electrode generated field which is at a maximum. Positive DEP is when a particle moves towards an electrode and negative DEP is when it moves away from an electrode into the center, which can be considered or visualized as a well.

FIG. 2D illustrates an example where a particle moves toward the center of the electrode field, and then returns back creating an angle of about 270 degrees.

Other electrode configurations can be used in combination with the proposed cross-over frequency measurement platform. One example is the inter-digitated design shown in FIG. 2C. Another example is the spiral design shown in FIG. 2D. The geometric shapes and inter-electrode spacings of the microelectrodes must be balanced or set for effective electric field gradient generation to induce motion in particles of different sizes ranging from about 10 nm to a few millimeters.

In a more specific example, a glass slide or other substrate containing the microelectrodes is placed on a microscope stage and observed using bright field or fluorescence microscopy. The motion of one or more particles may then be captured using a CCD camera mounted onto the microscope together with image acquisition software. In a cell or particle analyzer platform, a small volume of the fluid containing the suspended cells (cell suspension) or particles for observation is pipetted onto the active region of the microelectrodes. The sample volume can range from about 10 microliters up to about 500 microliters. Test cells (e.g., cell sample to be analyzed) or particles may be suspended in a fluid whose physico-chemical properties are chosen to maintain the integrity or viability of the particles. For mammalian cells, such physico-chemical properties include the pH, conductivity, chemical composition, tonicity, and osmolarity of the solution. The number and/or density of the suspended particles or cells is chosen to minimize the effects of particle-particle interactions, which means that the particles or cells have an average separation of no less than about two particle or cell diameters when viewed under the microscope.

Preferably, the software which controls the operation of the signal generator and camera has a graphical user interface (GUI). The GUI provides a means to enter identification parameters to distinguish a particular procedure and user. This screen provides the user with the ability to input operating parameters such as frequency, voltage, and hold time. A table containing values for frequency, voltage, and hold time values may be defined by the user to enable the particles of interest to undergo a transition from negative DEP (repulsive force) to positive DEP (attractive force) or vice versa. Initiating and/or terminating elements, such as push buttons, enable the user to initiate a test sequence of applied voltages to a sample, as well as to enable the user to abort the measurement sequence. Pop-up screens may be included to alert the user to the experimental parameter limits if they are mistakenly exceeded beyond those initially set or desired. A video of the procedure may also be displayed in the GUI, with the frequency information embedded in the video in real time. Camera settings, such as exposure time and camera gain, can be adjusted in the camera settings section of the software program. The software preferably generates an AVI file that is uncompressed or encoded with a particular code for image compression.

Preferably, in accordance with the present invention, the analysis software enables a captured video to be imported into the software for further examination. The software enables the user to mark individual particles recorded and manually track movement of the recorded particles through the entire course of the video, as the signal generator incrementally sweeps through a range of frequencies by, for example, joining the marked points with lines.

The software also preferably enables the user to perform time stepping by defining a step size depending on the velocity of the moving particle under observation. The displacement vector of the moving particle may be calculated and the change between the current displacement vector and previous displacement vector may also be calculated. An angular change of greater than about 270 degrees, preferably a reflex angle change of greater than 270 degrees to about 360 degrees, between two successive displacement vectors can be identified as a transition from negative to positive (or positive to negative) DEP.

At the exact value of the DEP cross-over frequency, the cell or particle does not exhibit DEP-induced motion. An accurate estimation of the value of the cross-over frequency is derived by determining the mid-value of the two applied voltage frequencies about which a reversal of the direction of particle motion was observed in the suspension or fluid medium. This analysis can be performed for one or more particles of the population of particles undergoing DEP-induced motions.

The sequence of the displacement vectors determined for each characterized particle are then preferably displayed as a continuous track on the computer monitor. This display of information provides the user with the means to observe which of the particles have progressed through a DEP cross-over event, and that is signified by the track tracing out approximately the shape of an arrow or arrow head-type image. The point of this arrow head represents the DEP cross-over frequency event.

Thus, for example, if a DEP cross-over point occurs at 100 kHz for a particular cell, and initially the voltage applied to the electrodes is lower (e.g., 80 kHz frequency) the cell(s) will be experiencing negative dielectrophoresis and they will be pushed away from the electrodes. Then once the voltage applied crosses the DEP cross-over point of 100 kHz, the cell(s) will be drawn toward the electrodes. By comparing the images of the cell(s) movement away and toward the electrodes, and performing the calculation as discussed herein, the identity of the DEP cross-over point for the cell(s) can be determined and that information can be conveyed to a user via, for example, the CPU unit and display monitor. Thus the method of the invention includes assessing the movement of particles and indicating at any point on the path of movement what the electric signal is and, in particular, identifying frequency at any particular point next to that particular point of travel of the cell. Thus, the method provides a quick and accurate way of getting the information a user or analyzer needs regarding what would be a particular or typical cross-over frequency of a particular cell type from a particular sample. This can be very helpful where, for example, the analysis has been conducted repeatedly to provide a large amount of arrow head-type data.

The method of the invention therefore provides a characteristic parameter of the of the electro-kinetic properties of a population of cells that can be used for various applications, including defining the frequency at which a DEP separation device should be set, or using the information to monitor how cells are changing their physiological state because, for example, they are dying or receiving a cytotoxic drug, or stem cells are differentiating, or after passages through a DEP separation device one can observe that cells are changing their phenotypes after a certain number of passages and therefore should be discarded. Thus, by determining the correct frequency at which to operate a DEP separation system one can obtain a high level of cell recovery or efficiency.

Thus, once the DEP cross-over frequency is determined in accordance with the present invention, one can determine what an accurate separation frequency of the desired particles is relative to the undesirable particles for application in a DEP separation device for a particular sample. Once the accurate DEP separation frequency is determined by the method of the invention, target sample particles may be efficiently separated from non-target sample particles because desired particles can be accurately and efficiently drawn towards an electrode while non-target particles are pushed away from the electrodes.

Software maybe be developed to carry out the method or publicly available software may be employed for tracking movements of particles such as cells, such as ImageJ®, which is publically available at hypertext transfer protocol:// rsbweb.nih.gov/ij/download.html.

The content of all patents, patent applications, published articles, abstracts, books, reference manuals and abstracts, as cited herein are hereby incorporated by reference in their entireties to more fully describe the state of the art to which the disclosure pertains.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variations that fall within the scope of the appended claims.

What is claimed is:

1. A system for determining a dielectrophoretic cross-over frequency of a target particle, the system comprising:
    a chamber configured to receive a sample containing a target particle;
    an electric field source comprising at least one electrode;
    a signal generator in electrical communication with the electrode, the signal generator configured to generate an electric field on the sample in a manner causing the target particle to move with respect to the at least one electrode, wherein the signal generator is configured to 1) adjust the electric field such that the target particle approximately pauses movement, and 2) further adjust the electric field such that the target particle changes direction and moves generally toward the at least one electrode, wherein the path of movement of the target particle creates a reflex angle; and
    an image recording device configured to record images of cells in the sample responding to the electric field, the images configured for identifying the path of movement of the target particle with respect to the at least one electrode, wherein the path of movement is used for identifying the dielectrophoretic cross-over frequency of the particle.

2. The system of claim 1, further comprising a microscope, wherein the chamber is positioned on the microscope, the microscope is configured to provide a magnified view of the target particle and the at least one electrode, and the image recording device is configured such that the recorded images are magnified images provided by the microscope.

3. The system of claim 2, wherein the microscope is an inverted fluorescence microscope.

4. The system of claim 2, wherein the at least one electrode is disposed on a substrate that is optically transparent, and the substrate is locatable on a platform within the chamber such that the target particle and the at least one electrode are in the magnified view.

5. The system of claim 4, wherein the at least one electrode is at least one of photolithographically patterned on the substrate, electroplated on the substrate, and laser ablated on the substrate.

6. The system of claim 5, wherein the substrate is constructed of a material selected from the group of glass and plastic.

7. The system of claim 4, wherein the at least one electrode comprises a plurality of planar microelectrodes.

8. The system of claim 7, wherein the plurality planar microelectrodes comprise gold coatings that are photolithographically patterned on a titanium seed layer, the titanium seed layer is metal vapor deposited on a planar surface of the substrate, and the substrate is constructed of glass.

9. The system of claim 8, wherein the gold coatings having a thickness of about 100 nm, and the titanium seed layer has a thickness of about 3 nm.

10. The system of claim 7, wherein the plurality of planar microelectrodes comprises interdigitated electrodes.

11. The system of claim 7, wherein the plurality of planar microelectrodes comprises intermeshed spiral electrodes.

12. The system of claim 7, wherein the plurality of planar microelectrodes comprises four planar microelectrodes spaced at 90-degree intervals about a central region.

13. The system of claim 12, wherein the four planar microelectrodes have inner portions facing the central region, and the inner portions each have a polynomial profile.

14. The system of claim 12, wherein the four planar microelectrodes have inner portions facing the central region, and the inner portions each have a semicircular profile.

15. The system of claim 12, wherein opposed pairs of the four planar microelectrodes have a spacing distance between the respective inner portions, and the spacing distance is in a range from about 100 microns to about 5 millimeters.

16. The system of claim 1, wherein the image recording device is a camera.

17. The system of claim 16, wherein the camera comprises at least one of a CCD sensor and a CMOS sensor.

18. The system of claim 1, further comprising a monitor in electrical communication with the image recording device, wherein the monitor is configured to display the recorded images.

19. The system of claim 18, further comprising a computer having a central processing unit (CPU), wherein the CPU is in electrical communication with the image recording device and the monitor, and the CPU is configured to execute software comprising image recognition software for tracking the path of movement of the target particle.

20. The system of claim 19, wherein the CPU is further configured to execute software for calculating displacement vectors of the target particle along the path of movement, creating a vector displacement diagram showing sequences of the displacement vectors, and displaying the vector displacement diagram on the monitor.

* * * * *